United States Patent
Bisogno

(10) Patent No.: US 6,953,342 B2
(45) Date of Patent: *Oct. 11, 2005

(54) COMPUTER PROGRAM, METHOD, AND SYSTEM FOR MONITORING NUTRITION CONTENT OF CONSUMABLES AND FOR FACILITATING MENU PLANNING

(76) Inventor: Joseph J. Bisogno, 16210 W. 110th St., Lenexa, KS (US) 66219

( * ) Notice: Subject to any disclaimer, the term of this patent is extended or adjusted under 35 U.S.C. 154(b) by 0 days.

This patent is subject to a terminal disclaimer.

(21) Appl. No.: 10/889,577

(22) Filed: Jul. 12, 2004

(65) Prior Publication Data

US 2005/0008994 A1 Jan. 13, 2005

Related U.S. Application Data

(63) Continuation of application No. 09/878,651, filed on Jun. 11, 2001, now Pat. No. 6,817,863.

(51) Int. Cl.$^7$ .......................... G09B 19/00; G06F 17/60
(52) U.S. Cl. .......................... 434/127; 235/375; 705/2; 128/921
(58) Field of Search .................................. 434/127, 238, 434/262; 128/897, 921; 235/375, 380, 383, 38; 600/300; 221/300, 2, 3, 15; 345/810, 901, 902; 700/90, 213; 705/1, 2, 15, 26; 707/1, 3, 104.1; 709/203, 217, 229

(56) References Cited

U.S. PATENT DOCUMENTS

| | | | |
|---|---|---|---|
| 4,464,122 A | 8/1984 | Fuller et al. | 434/262 |
| 4,611,466 A | 9/1986 | Keedy | |
| 5,301,645 A | 4/1994 | Ball et al. | |
| 5,673,691 A | 10/1997 | Abrams et al. | 600/300 |
| 5,836,312 A | 11/1998 | Moore | 128/897 |
| 5,841,115 A | 11/1998 | Shepley | 235/375 |
| 5,890,128 A | 3/1999 | Diaz et al. | 705/2 |
| 6,024,281 A | 2/2000 | Shepley | 235/375 |
| 6,095,949 A | 8/2000 | Arai | 434/127 |
| 6,356,940 B1 | 3/2002 | Short | 709/217 |
| 6,553,386 B1 | 4/2003 | Alabaster | 707/104.1 |
| 6,696,924 B1 | 2/2004 | Socinski | 221/15 |
| 6,817,863 B2 * | 11/2004 | Bisogno | 434/127 |

FOREIGN PATENT DOCUMENTS

| | | | |
|---|---|---|---|
| FR | 1463799 | 7/1966 | |
| JP | 11-154147 A * | 6/1999 | 434/127 |

* cited by examiner

*Primary Examiner*—Willis R. Wolfe, Jr.
(74) *Attorney, Agent, or Firm*—Hovey Williams LLP

(57) ABSTRACT

A computer program, method, and system for dynamically and interactively providing nutrition content information for consumables such that a user may monitor, tailor, plan, and review their intake thereof in light of a health-related interest or concern, such as, for example, weight-loss, food allergies, or diabetes or other nutrition affected illnesses or disabilities. Consumables are categorized and displayed in lists associated with an appropriate color to draw attention to relative nutrition content and to facilitate quicker and easier evaluation of a consumable of interest. Summaries are provided of a user's actual intake in light of a pre-established target intake for a particular day. Detailed reports may be generated showing consumption over a user-specifiable time period.

18 Claims, 5 Drawing Sheets

COMPUTER PROGRAM, METHOD, AND SYSTEM FOR MONITORING NUTRITION CONTENT OF CONSUMABLES AND FOR FACILITATING MENU PLANNING

RELATED APPLICATION

The present application is a continuation and claims priority benefit, with regard to all common subject matter, of earlier-filed U.S. patent application titled "COMPUTER PROGRAM, METHOD, AND SYSTEM FOR MONITORING NUTRITION CONTENT OF CONSUMABLES AND FOR FACILITATING MENU PLANNING", Ser. No. 09/878,651, filed Jun. 11, 2001 now U.S. Pat No. 6,817,863. The identified earlier-filed patent application is hereby incorporated into the present application by specific reference.

BACKGROUND OF THE INVENTION

1. Field of the Invention

The present invention relates to a computer program, method, or system for providing nutrition content information for consumables. More particularly, the present invention relates to a computer program, method, or method for dynamically and interactively providing nutrition content information for consumables such that a user may monitor, tailor, plan, and review their intake thereof in light of a health-related interest or concern, such as, for example, weight loss, food allergies, or diabetes or other nutrition-affected illnesses or disabilities.

2. Description of the Prior Art

It is often desirable to monitor nutrition content of consumables, including, for example, calories, fat, sugar, protein, or carbohydrates. This is particularly true where such nutrition content may affect a health-related interest or concern, including, for example, weight loss, food allergies, or diabetes or other nutrition-affected illnesses or disabilities. Relatedly, it is further desirable to plan future consumption based upon nutrition content, and to review past consumption summarized for a specifiable time period.

Various print resources exist to facilitate monitoring nutrition content. Books, for example, provide long lists of consumables and related nutrition information. Furthermore, most packaged consumables provide nutrition information on the packaging. Unfortunately, print resources suffer from a number of limitations and disadvantages. Books, for example, are bulky and difficult to conveniently tailor for efficient use by any particular person (short of adding or removing pages), which reduces likelihood of consistent use. Package-based information is, of course, limited to packaged foods. Furthermore, print resources are generally unable to practically present nutrition information in a visually descriptive manner operable to conveniently impart to a user a sense of a particular consumable's place in an overall monitoring scheme. Additionally, print resources are generally unable to practically provide a convenient mechanism whereby future consumption can be dynamically planned and past consumption can be reviewed.

It is known to use computers and computer programs to facilitate monitoring and planning intake of consumables. Existing programs, however, are typically non-interactive and non-dynamic and therefore inconvenient and awkward to use, which may decrease compliance and effectiveness. Furthermore, existing programs typically do not allow for substantial modification or customization to suit users' particular consumption habits or preferences, which may make the program inapplicable to or unuseable by some people or cultures.

Due to the above identified problems and shortcomings in the existing art, an improved computer program or method is needed for monitoring nutrition information of consumables and intake thereof.

SUMMARY OF THE INVENTION

The present invention provides a computer program, method, and system for dynamically and interactively providing nutrition content information for consumables such that a user may monitor, tailor, plan, and review their intake thereof in light of a health-related interest or concern, such as, for example, weight-loss, food allergies, or diabetes or other nutrition affected illnesses or disabilities. Nutrition content of interest may include, for example, protein, carbohydrates, fat, vitamins, minerals, calories, sugar, etc. Consumables are categorized according to a predetermined scheme of categorization, and the categories are displayed as scrollable and searchable lists. The lists are associated with an appropriate color to draw attention to the categories' relative nutrition content and to facilitate quicker and easier evaluation of a consumable of interest. Furthermore, menus may be planned in advance wherein projected intake of particular consumables is recorded. Additionally, summaries are provided of actual intake in light of a pre-established target intake for a particular day, week, month, or other user-specifiable time period.

The lists of consumables and associated nutrition content information are stored in a database customizable with regard to adding or deleting consumables and editing the nutrition content information. Thus, the user is able to adapt the program to more personally reflect their eating habits and preferences. For example, a user who does not eat meat may delete all meat items from the database in order to make finding and selecting non-meat consumables more convenient; and a user who uses low-fat or no-sugar ingredients or who reduces calories by baking rather than frying may edit the nutrition content information to reflect the change. Furthermore, users from different cultures may tailor the database to include consumables specific to that culture.

As mentioned, the consumables are categorized according to a predetermined scheme of categorization based upon the user's health-concern or interest. For example, where the user desires to monitor calorie and fat content to facilitate weight loss, the consumables may be divided into three groups—low, medium, and high calorie and fat content—and the groups associated with an appropriately recognizable display color, such as green for low or safe or desirable, yellow for medium or warning, and red for high or dangerous or generally undesirable with regard to the nutrition content of interest, to facilitate the user's recognition and understanding of any particular consumable's effect, relative to other consumables, on the user's goals.

Though the computer program and method may be implemented on any computing device, including, for example, a desktop or laptop personal computer, in a preferred embodiment the computer program is stored on and executed by a small, portable, battery-power, dedicated hand-held device. Because the small hand-held device is more conveniently and less conspicuously carried than a conventional desktop of laptop computer, the user is more likely to enter more consumption data at the time of consumption or shortly thereafter, thereby greatly increasing proper and consistent use of the present invention.

These and other advantages of the present invention are further described in the section entitled DETAILED DESCRIPTION OF A PREFERRED EMBODIMENT, below.

BRIEF DESCRIPTION OF THE DRAWING FIGURES

A preferred embodiment of the present invention is described in detail below with reference to the attached drawing figures, wherein.

DETAILED DESCRIPTION OF A PREFERRED EMBODIMENT

Figure 1:
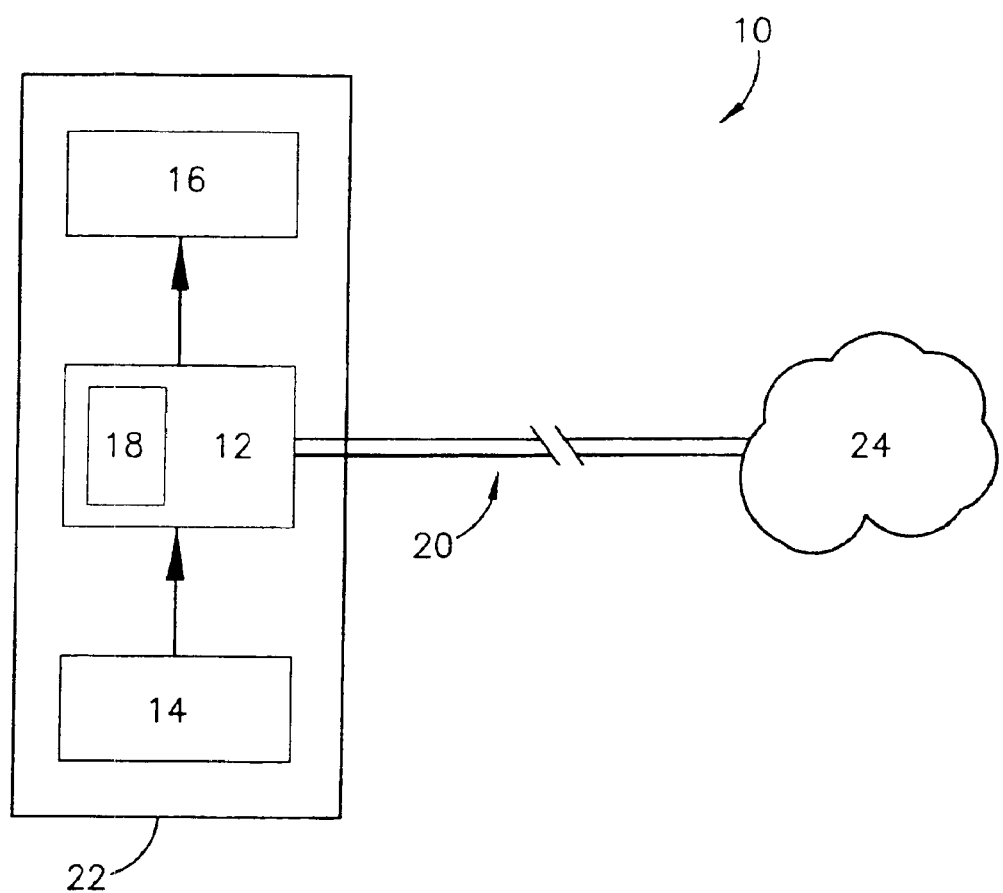
FIG. 1 is a block diagram depicting a system or apparatus that may be used to implement a preferred embodiment of the present invention.

FIG. 1 illustrates a preferred embodiment of a system 10 for dynamically and interactively providing nutrition content information for consumables such that a user may monitor, tailor, plan, and review their intake thereof in light of a health-related interest or concern, such as, for example, weight loss, diabetes or other nutrition affected illnesses, or food allergies.

The preferred system 10 broadly comprises a processor 12; an input device 14; an output device 16; a memory 18; and a network connection 20. The system 10 is independent of any specific nature or details of its various components so long as the combination thereof is operable to practice the invention as herein described. Thus, the system 10 may, for example, be a conventional desktop personal computer, a conventional portable laptop or notebook computer, or a conventional networked thin-client terminal. Alternatively, the system 10 may be a portable, exclusively battery-powered, hand-held dedicated device enclosed within a housing 22 and specifically adapted to practicing the present invention. This latter embodiment is advantageous in that the resulting device is smaller and less expensive than the conventional devices previously mentioned, and allows the present invention to be more conveniently carried and practiced, thereby increasing likelihood and frequency of use.

The processor 12 may be any suitable conventional processing device operable to receive input from the input device 14, consult a database of consumables and related nutrition content information, and report results via the output device 16.

The input device 14 allows the user to provide input to the processor 12. Such input may include login or identification information; target consumption values; and consumables already or prospectively consumed. As mentioned, the exact nature and details of the input device 14 are generally unimportant to the present invention, and may depend greatly upon the nature of the system 10. For example, a general-purpose conventional computer system may provide a variety of suitable input devices, including a keyboard, a computer mouse or trackball, a light pen, or a touch screen. A hand-held dedicated system or apparatus may be more limited in the types of input devices able to be supported, and may be limited to a stylus-type instrument.

The output device 16 visually and dynamically communicates information to the user. The output device 16 is preferably a screen of some suitable type, such as, for example, a conventional computer monitor or a liquid crystal display.

The memory 18 and network connection 20 are alternative or complimentary mechanisms for storing/accessing the computer program of the present invention. In some embodiments, only the memory 18 is included, it being operable to store the program, including the database of consumables, in its entirety. Any suitable memory 18 may be used, including a hard disk, a floppy disk, a compact disk, or a read only memory chip. In other equally preferred embodiments, only the network connection 20 is included, it being operable to provide access via a communication network 24 (e.g., a local area network, a wide area network, or the Internet) to the program, wherein the program is remotely stored. In still other equally preferred embodiments, both the memory 18 and the network connection 20 are included. In these latter embodiments, a first portion of the program may be stored in the memory 18 and a second portion, possibly the database of consumables, may be accessed via the network connection 20 and communication network 24.

The computer program comprises a combination of code segments accessible to and executable by the processor 12 of the above-described system 10, and operable to facilitate monitoring, tailoring, planning, and reviewing intake of consumables based upon nutrition content in light of a health-related interest or concern. The code segments may be written in any programming language, including JAVA or C++, as a matter of design choice, and stored on any suitable computer readable memory media, such as, for example, a hard disk, a floppy disk, a compact disk, or a read only memory chip.

The preferred computer program broadly comprises a database (or a code segment to access such) of consumables and related nutrition content information; a code segment operable to generate an interactive display screen for display on the output device 16; a code segment providing for prospective menu planning; and a code segment for generating summaries of past consumption over a user specifiable time period.

The database serves as a repository of the nutrition content information, which may be implemented as single large general data repository or a plurality of smaller linked data-specific databases, and, as mentioned above, may be stored in the memory 18 forming a part of the system 10 or may be located in and accessed from one or more remote memory storage devices. Where the database is remotely located, access thereto is preferably accomplished via the communications network 24, such as the Internet.

Preferably, the user is able, as desired, to edit information stored in the database, at least with regard to how the database appears to the particular user. Such editing may include, for example, adding or delete consumables, or changing nutrition content information. Thus, the database is customizable to the particular user's consumption habits, allowing the user to adapt the program to more personally reflect their eating habits and preferences. For example, a user who does not eat meat may delete all meat items from the database in order to make finding and selecting non-meat consumables more convenient; and a user who uses low-fat or no-sugar ingredients or who reduces calories by baking rather than frying may edit the nutrition content information to reflect the change. Furthermore, users from different cultures may tailor the database to include consumables specific to that culture.

The code segment operable to generate an interactive display screen is also operable to present scrollable or drop-down lists of consumables, wherein the consumables have been categorized according to a predetermined scheme of categorization based upon the particular health-related concern or interest. The lists are displayed associated with a color appropriate to facilitate the user's easy understanding and evaluation of a consumable of interest. For example, where the user desires to monitor calorie and fat content to facilitate weight loss, the consumables may be divided into three groups—low, medium, and high calorie and fat content—and the groups associated with an appropriately recognizable color, such as green for low or safe, yellow for medium or warning, and red for high or dangerous, to facilitate the user's recognition and evaluation of any particular consumable's effect, relative to other consumables, on the user's goals. This particularly advantageous feature places each consumable into a larger context rather than presenting mere sterile information devoid of context. Thus, the present invention's use of color-based presentation allows for a conveniently intuitive evaluation of a consumable of interest.

The code segment providing for prospective menu planning allows the user to select a desired date, set a target value representing a maximum threshold intake of one or more nutrients, and plan and store a menu of consumption for the selected day.

The code segment for generating historical summaries allows the user to review past consumption and nutrient intake over a user-specifiable time period, such as a day, week, month, or year. This advantageous feature allows the user to review their compliance and progress toward achieving their health-related goal.

Figure 2:
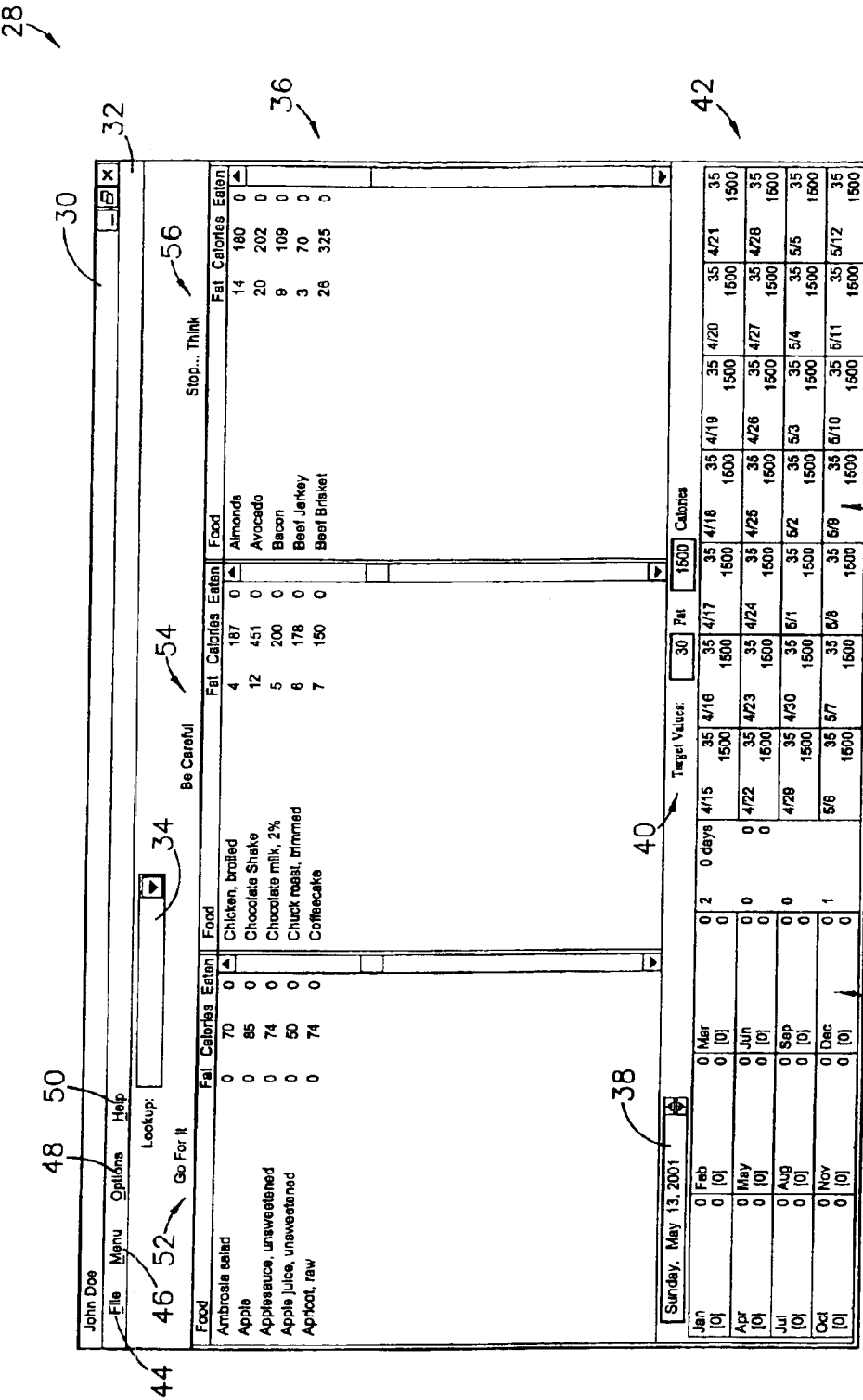
FIG. 2 is a first screen capture showing a first preferred interface screen generated by a preferred embodiment of a computer program of the present invention.

Referring also to FIG. 2, the Interface Screen 28 provides a visual mechanism facilitating user interaction with the computer program, and comprises a Title Bar 30; a Menu Bar 32; a Lookup Box 34; a plurality of Food Categories 36; a Date Field 38; a Target Section 40; and a Summary Section 42.

The Title Bar 30 identifies the computer program and the current user, which is particularly useful where two or more persons use the same instance of the program on the same system 10. The identity information displayed in the Title Bar 30 is provided by the current user who is required to login at the beginning of each session. The login requirement allows the program to record custom parameters selected by the current user during the current session and retrieve any previously select customs parameters; such parameters may include display preferences and edits to the list of consumables and nutrition content.

The Menu Bar 32 presents four menu anchors selectable to display drop-down menus of selectable functions. The four menu anchors correspond to a File menu 44; a Menu menu 46; an Options menu 48, and a Help menu 50.

The File menu is a drop-down menu presenting a number of selectable functions, including Select Person; Add New Person; Delete Person; Print Report; Preview Report; Printer Setup; and Exit. The Select Person function causes a list of previously registered users to appear from which the current user may select him or herself, thereby making the login process more convenient. The Add New Person function allows the user, if not previously registered, to login for the first time. Thereafter, to login the user may simply select him or herself from the Select Person list. The Delete Person function allows a previously registered user to be deleted such that their name will no longer appear on the Select Person list. The Print Report, Preview Report, and Printer Setup are all conventional functions related to printing reports and summaries of past consumption. The Exit function is conventionally operable to exit the computer program.

Figure 4:
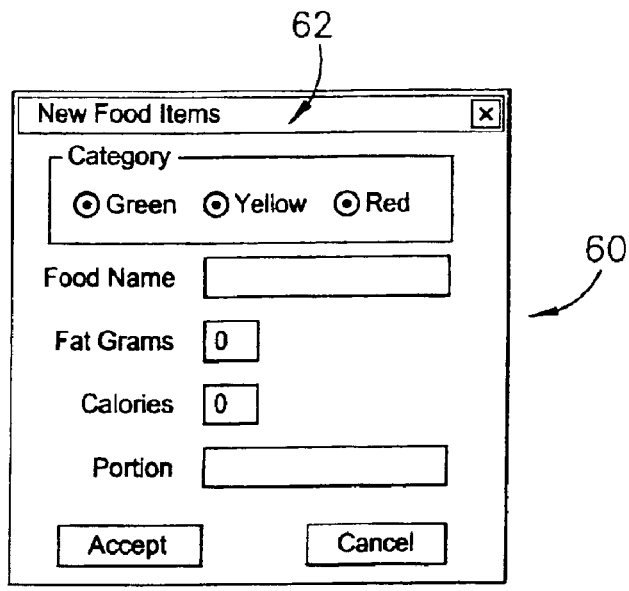
FIG. 4 is a third screen capture showing an input window generated by a preferred embodiment of a computer program of the present invention.

The Menu 46 is a drop-down menu presenting a number of selectable functions, including Add 1; Remove 1; Delete Item; Revise Item; New Food Item. The Add 1 function causes one instance of a particular consumable, which is highlighted in the scrollable lists, to be added to the intake record. The Remove 1 function causes one instance of a particular consumable, which is highlighted in the scrollable lists, to be removed from the intake record. The Delete Item function causes a highlighted consumable to be deleted from the scrollable lists, thereby making customization of the consumables database or corresponding lists more convenient. The Revise Item and Add New Food Item functions are similar in that each produces an interactive window 60 (see FIG. 4) wherein a consumable's name, nutrition content, and portion size may be edited or added in corresponding data fields, and the consumable may be reassigned to a different grouping or scrollable list. This latter reassignment may be conveniently accomplished using selectable radio buttons 62 corresponding to the various groups or lists. The Revise Item and Add New Item functions are distinguishable in that the Revise Item function applies to consumables already present in the database such that the data fields are initially filled with existing, editable data, whereas, using the Add New Item function, the data fields are blank.

Figure 6:
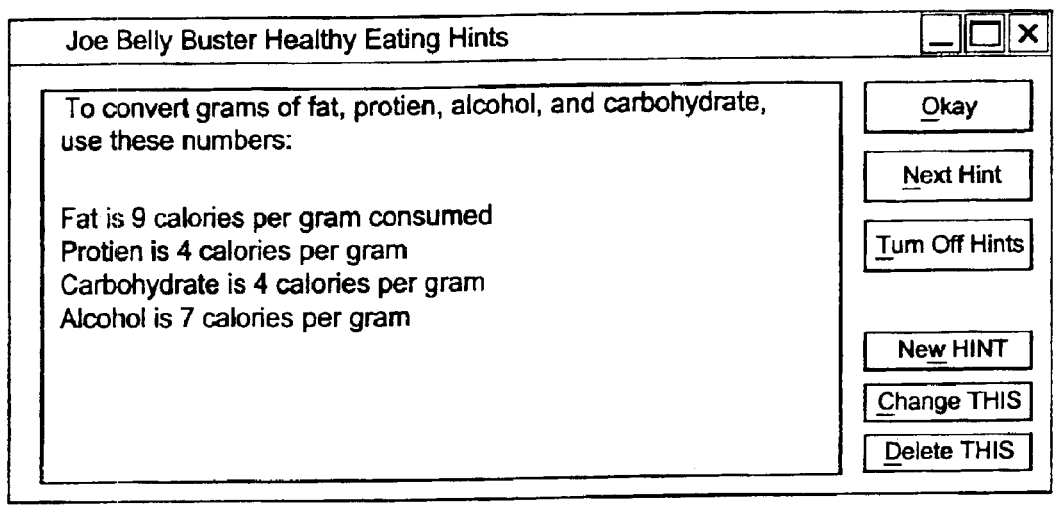
FIG. 6 is a fifth screen capture showing a hint window generated by a preferred embodiment of a computer program of the present invention.

The Options menu 48 is a drop-down menu presenting a number of selectable functions, including Counts, Remaining, and Show Hints. The Counts and Remaining functions toggle the display between, respectively, total nutrition content value consumed and percentage of total nutrition content value remaining for consumption relative to the pre-established Target Values (where the Target Values represent 100%). The Show Hints function, when selected, causes a hint window 68 to appear that communicate consumption and nutrition tips (see FIG. 6). The tips are preferably editable so that the user may customize the tips to their own needs.

Figure 5:
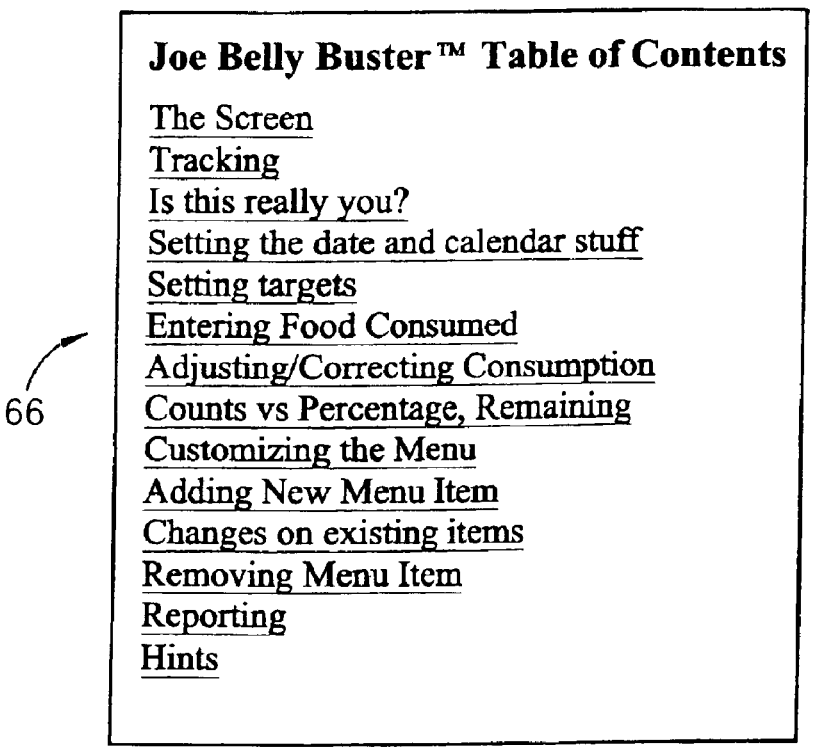
FIG. 5 is a fourth screen capture showing a help window generated by a preferred embodiment of a computer program of the present invention.

The Help menu 50 is a drop-down menu presenting a number of selectable functions, including Help. The Help function causes a conventional help screen 66 to appear with which the user may learn about the present invention and investigate particular functions (see FIG. 5).

The Lookup Box 34 allows a user to quickly find consumables in the lists. In use, a user begins typing the name of the consumable into the Lookup Box 34; as letters are typed, the box 34 actively matches those letters to a drop down menu of similarly named consumables, thereby displaying consumables whose spelling matches the user input. At any point the user may finish entering the consumable's name or select it from the drop down menu. Once entered in the Lookup Box 34, the consumable becomes the active item in the Food Categories 36.

The plurality of Food Categories 36 are scrollable lists 52,53,56 of consumables grouped according to one or more predetermined characteristics, such as, for example, nutrition value, calorie values, or fat values. In the illustrated embodiment, for example, consumables are divided into three groups—low, medium, and high calorie and fat content—and the groups are displayed in scrollable lists 52,54,56 wherein each group is associated with an appropriately recognizable color, such as green for low or safe, yellow for medium or warning, and red for high of dangerous, to facilitate the user's recognition and evaluation of any particular consumable's effect, relative to other consumables, on the user's goals.

Also in the preferred embodiment, the lists 52,54,56 are labeled Go For It, Be Careful, and Stop . . . Think. The Go For It category 52 presents a columnar scrollable list of selectable consumables which are generally desirable, being, for example, low in calories and fat. Because the color green is generally associated with the concept of safety, the list is preferably highlighted or otherwise indicated in green.

The Be Careful category 54 presents a columnar scrollable list of selectable consumables for which caution should be observed, they being higher in calories and fat than those in the previous category. Because the color yellow is generally associated with the concept of caution, the list is preferably highlighted or otherwise indicated in yellow.

The Stop . . . Think category 56 presents a columnar scrollable list of selectable consumables for which a great deal of consideration should be given prior to consumption, they being even higher in calories and fat than those in the previous categories and generally undesirable or unsafe with regard to the nutrition content of interest. Because the color red is generally associated with the concept of danger, the list is preferably highlighted or otherwise indicated in red.

The Date Field 38 facilitates tracking consumption on a daily basis. The Date Field 38 defaults to the current date when the program is executed, and can thereafter be adjusted to reflect any date the user desires. The Date Field 38, in conjunction with the Summary Section 42 described below, facilitates menu planning over an extended period of time, including days or weeks.

The Target Section 40 allows the user to set their own personal daily target values for nutrients, such as grams of fat and calories consumed. The target values provide threshold means for determining whether the user's intake goals have been met.

Figure 3:
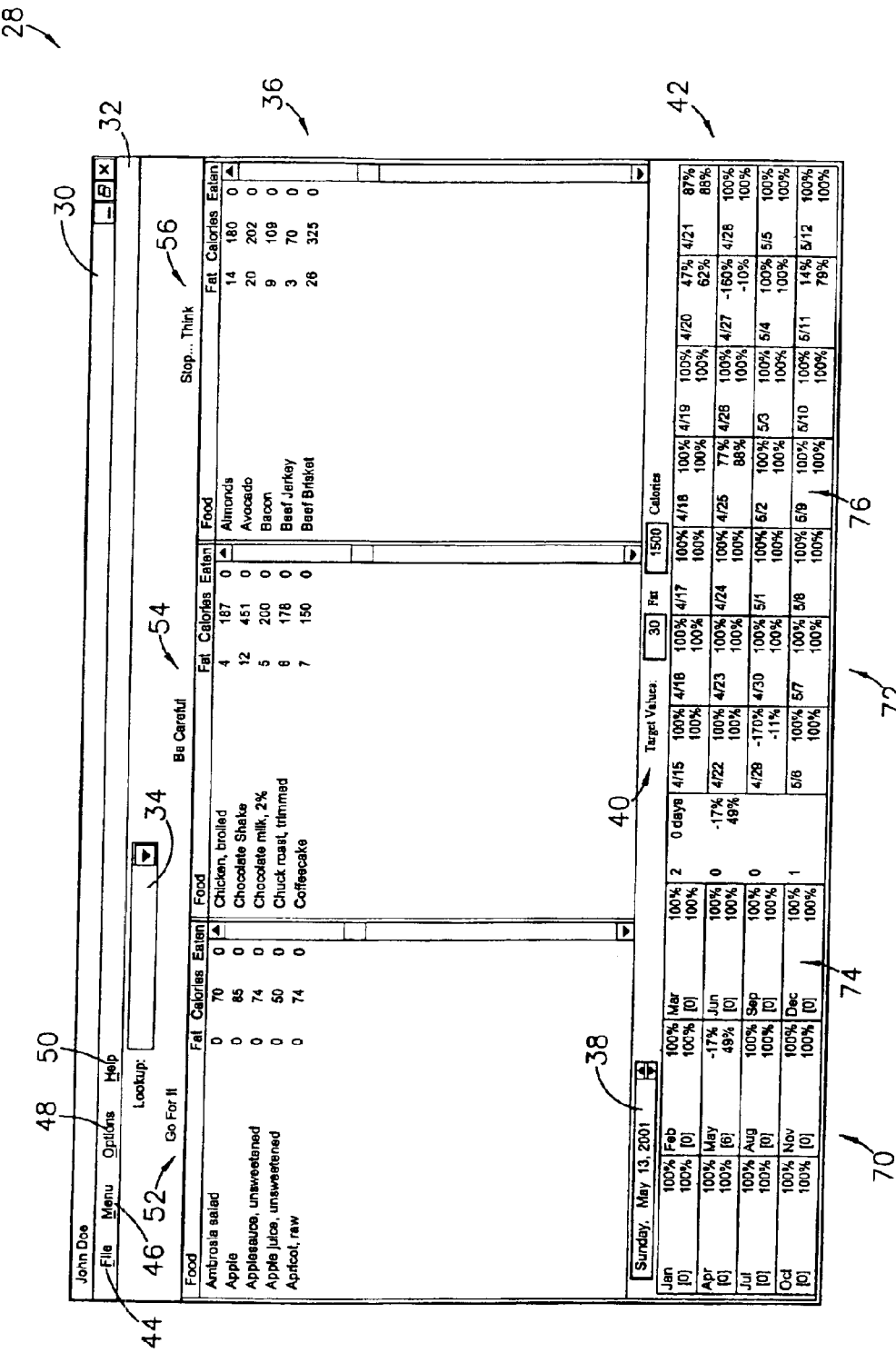
FIG. 3 is a second screen capture showing a second preferred interface screen generated by a preferred embodiment of a computer program of the present invention.

The Summary Section 42 comprises two calenderic tables, a Month table 70 and a Day table 72. The Month Table 70 includes twelve month cells 74, with each month cell 74 corresponding to a particular month of a year. Each month cell 74 contains four items, including the first three letters of the name of the month (e.g., Jan for January); the number of days of that month for which consumption data has been entered; and a fat value and a calorie value displayed in either "Count" or "Remaining" formats. In Count format, the fat and calorie values are displayed as Total Target minus Total Consumed, wherein Total Target is calculated as the daily Target Value multiplied by the number of days for which data has been entered. In Remaining format, the fat and calorie values are similarly calculated though displayed as percentages, wherein Total Target is 100%. In either format, when Total Consumed fat or calories exceeds Total Target, the value is displayed in red to draw attention and indicate a violation of the Target Values. The Summary Section 42 of FIG. 2 illustrates the Count format; the Summary Section 42 of FIG. 3 illustrates the Remaining format.

The Day Table 72 includes twenty-eight day cells 76 (four rows of seven columns), with each day cell 76 corresponding to a particular day of a month. Each day cell 76 contains three items, including the month and day, and a fat value and a calorie value displayed in either "Count" or "Remaining" formats. The display formats are substantially similar to those described above. In the Day Table 72, however, Total Target is merely the Target Value, rather than a multiple thereof. Where Total Consumed exceeds Total Target, the values are displayed in red.

For example, initially, each month cell 74 in the Month Table 70 reflects no fat consumed and no calories consumed. If the user were to enter a target fat value of 35 and a target calorie value of 1800, each cell 76 in the Day Table 72 would automatically change to reflect these Target Values. Subsequently, as the user enters consumption data for a particular date, the fat and calorie values in that day cell 76 change to reflect the consumption in light of the Target Values. Furthermore, the corresponding month cell 74 will change, as described above, to reflect that data has been entered for a day of that month.

The Month and Day Tables 70,72 provide convenient quick summaries of consumption patterns over time. They also facilitate menu planning in that, upon adding an item to the consumption record, the user is immediately shown the effect of the addition on their consumption goal. This is particularly helpful where the addition of a particular item would cause total consumption to exceed Target Values for that time period.

With regard to the nature of the input device 14, the Interface Screen 28 can be navigated and operated using a keyboard, mouse, stylus, or other similar input device. Using a keyboard, the menu items can be accessed through the Alt-F(ile), Alt-M(enu), Alt-O(ptions) and Alt-H(elp). Conventional hot key techniques can be used to select drop down menus or particular functions from the drop down menus. The main screen 28 is organized as a collection of tab stop addresses. Initial stop is the green list 52, followed by the yellow list 54, and the red list 56, then the Date Field 38, the Target Section 40, and finally the Lookup Box 34 from which the tab stop cycle repeats. Within the lists 52,54,56, the keyboard's up and down arrows allow scrolling through the list 52,54,56, and the enter key allows the user to change the consumption count. Within the Date Field 38, the right and left arrow keys navigate among subfields, and up and down arrow keys change values.

In operation, a user is first asked to identify him or herself, either by selecting their name or identifier from a list of registered users, or by creating a new registration. This feature enables the program to store and display user-specific information, including, for example, Target Values, planned menus, and summaries of past consumption. The current user's name will appear in the Title Bar 30.

The program defaults to the current date; however, any desired date may be entered in the Date Field 38 or selected from the calenderic Summary Section 42. This feature is particularly useful where the user has not entered data on a daily basis and seeks to update their consumption history.

Upon start-up, a diet tip or hint is presented. The user may ask for additional hints, or turn off the hint feature. Furthermore, the user may alter, add, or remove diet hints, as desired.

The user may then set, in the Target Section 40, nutrition Targets Values for that date. In the illustrated example, calorie and fat content are the values of interest. The Target Values are used as threshold values in the consumption summaries.

Once the Target Values are set, the user may proceed to investigate consumables from the scrollable lists 52,54,56.

When the user cannot find a particular consumable in the lists 52,54,56 or finds that the lists 52,54,56 are inconveniently cluttered with consumables infrequently or never consumed, the user may add a consumable to or delete a consumable from the database. This feature is useful for adapting the database to the user's eating preferences and habits. In extreme situations, the entire existing database may be deleted and a variety of alternative consumables added. Thus, for example, the program can be easily adapted to be applicable to any person of any culture in any city or region of any country. Similarly, the user may change the nutrition content information for a particular consumable. This latter feature is particularly useful where ingredients, preparation, or serving size has been changed to result in a consumable having different nutrition characteristics.

The user may select a particular consumable from the lists 52,54,56 by double-clicking it or highlighting it and selecting Add 1 from the Menu menu 46 to indicate that one or more instances of the consumable has been or will be consumed. The selected consumable and its associated nutrition information is then added to the consumption history. The user may also remove or deselect an inadvertently or mistakenly selected consumable by highlighting it and selecting Remove 1 from the Menu menu 46.

As the user enters or edits consumption data for a particular date, the fat and calorie values in that day cell 76 change to reflect the consumption in light of the Target Values. Furthermore, the corresponding month cell 74 will change, as described above, to reflect that data has been entered for a day of that month.

At any time, the user may preview or print a report of consumption over a specified time period, such as, for example, a day, week, month, or year. The program may be set to format the report based upon menu order, date order, or other ordering interest. The report provides greater detail, including a breakdown of consumables, than the summarized information provided in the Summary Section 42.

From the preceding description, it can be appreciated that the present invention provides a computer program and method for dynamically and interactively providing nutrition content information for consumables such that a user may monitor, tailor, and plan their intake thereof in light of a health-related interest or concern, such as, for example, weight loss, diabetes or other nutrition affected illnesses, or food allergies. Although the invention has been described with reference to the preferred embodiment illustrated in the attached drawings, it is noted that equivalents may be employed and substitutions made herein without departing from the scope of the invention as recited in the claims. Those skilled in the art will appreciate, for example, that though described herein in terms of menu planning, wherein calorie and fat intake is of prime consideration, the present invention has application to menu planning wherein other food characteristics are emphasized. For example, an equally preferred version of the present invention may be tailored to menu planning for persons with particular allergies; illnesses, such as diabetes; or disabilities affected by the consumption of certain foods.

Having thus described the preferred embodiment of the invention, what is claimed as new and desired to be protected by Letters Patent includes the following:

1. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein the health-related concern is selected from the group consisting of the following: caloric content, protein content, carbohydrate content, fat content, vitamin content, mineral content, sugar content.

2. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein input device is operable to allow the user to customize the database based on a consumption habit.

3. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein the hand-held apparatus is powered exclusively by one or more cells or batteries.

4. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein the input device is a stylus.

5. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein the input device is a touch screen.

6. A hand-held apparatus for providing nutrition content information, the hand-held apparatus comprising:

a housing;

a computer-readable memory located within the housing and storing a combination of code segments and a database including consumables and related nutrition content information;

a processor located within the housing and operable to execute the combination of code segments and access the database to sort the consumables into a plurality of lists corresponding to a health-related concern;

an output device incorporated into the housing and operable to display an interactive display screen generated by the combination of code segments, the interactive display screen presenting the lists and a remaining consumption value; and an input device coupled with the processor and operable to allow a user to select a particular consumable from the lists and to enter a target consumption value corresponding to a maximum future intake of one or more nutrients, whereupon the processor determines the remaining consumption value based on the difference between the target consumption value and the related nutrition content information of each selected consumable; and wherein the output device is a liquid crystal display.

7. A computer program comprising a combination of code segments stored in a computer-readable memory and executable by a processor to provide nutrition information, the computer program comprising:

a database including consumables and related nutrition content information;

a code segment operable to receive an input relating to a health-related concern;

a code segment operable to sort the consumables into a plurality of scrollable lists based on the input and the nutrition content information; and a code segment operable to display the lists;

further including a code segment operable to customize the database based on a consumption habit.

8. The computer program as set forth in claim 7, wherein the health-related concern is selected from the group consisting of the following: caloric content, protein content, carbohydrate content, fat content, vitamin content, mineral content, sugar content.

9. A computer program comprising a combination of code segments stored in a computer-readable memory and executable by a processor to provide nutrition information, the computer program comprising:

a database including consumables and related nutrition content information;

a code segment operable to receive an input relating to a health-related concern;

a code segment operable to sort the consumables into a plurality of scrollable lists based on the input and the nutrition content information;

a code segment operable to display the lists; and wherein each of the lists is associated with a color to aid a user in evaluating the relative effect of consumables in the list with regard to the health-related concern.

10. The computer program as set forth in claim 9, further including a code segment operable to receive login information identifying a user, and recalling, based upon the login information, a user data set of specific user information.

11. The computer program as set forth in claim 9, wherein the database is accessible through a computing network.

12. A computer program comprising a combination of code segments stored in a computer-readable memory and executable by a processor to provide nutrition information, the computer program comprising:

a database including consumables and related nutrition content information;

a code segment operable to receive an input relating to a health-related concern;

a code segment operable to sort the consumables into a plurality of scrollable lists based on the input and the nutrition content information;

a code segment operable to display the lists; and further including a code segment operable to accept a target consumption value corresponding to a maximum future intake of one or more nutrients.

13. The computer program as set forth in claim 12, further including a code segment operable to allow a user to select at least one of the consumables from the lists.

14. The computer program as set forth in claim 13, further including a code segment operable to determine and display a remaining consumption value based on the difference between the target consumption value and the related nutrition content information of each selected consumable.

15. A computer program comprising a combination of code segments stored in a computer-readable memory and executable by a processor to provide nutrition information, the computer program comprising:

a database including consumables and related nutrition content information;

a code segment operable to receive an input relating to a health-related concern;

a code segment operable to sort the consumables into a plurality of scrollable, color-associated lists based on the input and the nutrition content information;

a code segment operable to customize the database based on a consumption habit;

a code segment operable to allow the user to select at least one of the consumables from the lists;

a code segment operable to accept a target consumption value corresponding to a maximum future intake of one or more nutrients;

a code segment operable to determine a remaining consumption value based on the difference between the target consumption value and the related nutrition content information of each selected consumable; and a code segment operable to display the lists and the remaining consumption value.

16. The computer program as set forth in claim 15, further including a code segment operable to receive login information identifying a user, and recalling, based upon the login information, a user data set of specific user information.

17. The computer program as set forth in claim 15, wherein the database is accessible through a computing network.

18. The computer program as set forth in claim 15, wherein the health-related concern is selected from the group consisting of the following: caloric content, protein content, carbohydrate content, fat content, vitamin content, mineral content, sugar content.

* * * * *